(12) United States Patent
Roux et al.

(10) Patent No.: US 8,855,263 B2
(45) Date of Patent: *Oct. 7, 2014

(54) METHOD AND APPARATUS FOR DETERMINING VOLUME FRACTIONS IN A MULTIPHASE FLOW

(71) Applicant: Schlumberger Technology Corporation, Sugar Land, TX (US)

(72) Inventors: Gilles Roux, Sainte Genevieve des Bois (FR); Roman Korkin, Berdsk (RU); Lev Zakharov, Bergen (NO)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,079

(22) Filed: Jun. 18, 2013

(65) Prior Publication Data

US 2013/0282305 A1 Oct. 24, 2013

Related U.S. Application Data

(63) Continuation of application No. 12/682,809, filed as application No. PCT/US2008/081732 on Oct. 30, 2008, now Pat. No. 8,472,582.

(60) Provisional application No. 60/983,894, filed on Oct. 30, 2007.

(51) Int. Cl.
*G01N 23/06* (2006.01)
*G06F 19/00* (2011.01)

(52) U.S. Cl.
CPC .............. *G06F 19/703* (2013.01); *G01N 23/06* (2013.01)
USPC ............................................... 378/53; 378/51

(58) Field of Classification Search
CPC .............................. G01N 23/06; G06F 19/703
USPC ................................................ 378/51-54, 57
See application file for complete search history.

(56) References Cited

U.S. PATENT DOCUMENTS 5,854,820 A 12/1998 Slijkerman et al.
6,028,992 A 2/2000 Henriot et al.
(Continued)

FOREIGN PATENT DOCUMENTS

EP 0236623 9/1987
(Continued)

OTHER PUBLICATIONS

International Preliminary Report on Patentability of the International Searching Authority mailed May 4, 2010.
International Search Report of the International Searching Authority mailed Jan. 16, 2009.

*Primary Examiner* — Courtney Thomas
(74) *Attorney, Agent, or Firm* — Cameron R. Sneddon; Lee Eubanks

(57) ABSTRACT

A method, apparatus and computer program product for measuring a composition of a multiphase fluid, including radiating a photon beam through the multiphase fluid and measuring radiation absorption by the multiphase fluid for at least three energy levels to obtain measured radiation absorption data, and providing the measured radiation absorption data to processing unit configured to calculate the composition of the multiphase fluid using the measured radiation absorption data, whereby an effect of an injected fluid on the absorption of the photon beam is taken into account during calculation of the composition of the multiphase fluid.

11 Claims, 5 Drawing Sheets

(56) References Cited

U.S. PATENT DOCUMENTS

| | | |
|---|---|---|
| 6,335,959 B1 | 1/2002 | Lynch et al. |
| 7,676,344 B2 | 3/2010 | Chevalier et al. |
| 8,472,582 B2 * | 6/2013 | Roux et al. .................. 378/53 |
| 2007/0144268 A1 | 6/2007 | Atkinson |
| 2007/0234780 A1 | 10/2007 | Gysling et al. |
| 2009/0000390 A1 | 1/2009 | Duhanyan et al. |

FOREIGN PATENT DOCUMENTS

| | | |
|---|---|---|
| EP | 0896666 | 2/1999 |
| WO | 94/25859 | 11/1994 |
| WO | 2008/060192 | 5/2008 |
| WO | 2008/107181 | 9/2008 |
| WO | 2009/093927 | 7/2009 |

* cited by examiner

METHOD AND APPARATUS FOR DETERMINING VOLUME FRACTIONS IN A MULTIPHASE FLOW

CROSS-REFERENCE TO RELATED APPLICATIONS

This application is a continuation of co-pending U.S. patent application Ser. No. 12/682,809 filed Jun. 7, 2010, which claims benefit of priority to PCT/US08/081,732 filed Oct. 30, 2008, which claims benefit of priority to U.S. Provisional Patent Application Ser. No. 60/983,894 filed Oct. 30, 2007, the applications of which are herein incorporated by reference.

BACKGROUND

1. Field of the Invention

The present invention generally relates to a method and apparatus for measuring the composition of a multiphase fluid, and more particularly to a method and apparatus for measuring the composition of a multiphase fluid using a radiation source.

2. Description of the Related Art

In industrial applications that involve flowing fluids, such as slurries, liquids, chemical, paper, pulp, petroleum, gas, pharmaceutical, food, mining, minerals and vapors and gasses in refinery, it is sometimes beneficial to know certain characteristics of the flowing fluids. For example, in the petroleum industry in which crude oil production is measured each day on its way from the well heads to the refineries, the volumetric flow rate can be an important measurement in process control and optimization.

Several techniques exist for measuring the composition of multiphase fluids by radiating a photon beam through a cross-section of the fluid. Typically, the photon beam is generated by an X-ray tube or chemical radioactive source. These techniques take into account that the absorption of photon beam radiation in a material (including fluids) can be expressed by the following formula:

$$I = I_o e^{-\mu x}$$

where Io is the intensity of the generated radiation (i.e., the intensity of the radiation generated by the radiation source), I is the intensity of the transmitted radiation (i.e., the intensity of the radiation detected by the detector after the radiation has passed through the material), $\mu$ is the linear attenuation coefficient of the material, and x is the transmission length of the radiation through the material (which can be a multiphase fluid).

These techniques also take into account that at a specific radiation energy level each material has a specific linear attenuation coefficient and that the linear attenuation coefficient varies in a predictable manner for the material when the radiation level is varied.

International Patent Application No. PCT/EP 94/01320 (published as WO 94/25859) discloses a method for measuring the composition of a multiphase fluid by transmitting a photon beam through the multiphase fluid and detecting the level of radiation absorption at two radiation energy levels. Using the detected levels of radiation (i.e., I) at two energy levels in combination with the assumption that the sum of the three phase fractions in the multiphase fluid, namely, oil, water and natural gas equals to one, produces a set of three linear equations with three unknowns (i.e., the phase fractions of oil, the phase fraction of natural gas, and the phase fraction of water). The set of linear equations is then solved using known techniques to obtain the fluid composition (i.e., the phase fractions of oil, the phase fraction of natural gas, and the phase fraction of water).

European Patent No. 0 236 623 discloses a method for measuring the composition of a multiphase fluid by transmitting a photon beam through the multiphase fluid and detecting the level of radiation absorption at three radiation energy levels. In addition, European Patent No. 0 236 623 discloses a method for calculating the multiphase fluid composition that takes into account radiation absorption caused by sand particles entrained in the multiphase fluid mixture and the sulfur content of the crude oil produced. Information related to radiation absorption caused by the sand and/or sulfur content is obtained using additional radiation systems, which radiate photon beams at energy levels distinct from the energy levels used to determine radiation absorption for the natural gas, water, and oil phase fractions in the multiphase fluid.

European Patent No. 0 896 666 discloses a method for measuring the composition of a multiphase fluid by transmitting a photon beam through the multiphase fluid and detecting the level of radiation absorption at three radiation energy levels. The method disclosed in European Patent No. 0 896 666 takes into account the effect of the salt content in the water fraction on the transmitted radiation (i.e., I).

SUMMARY

The present invention includes the recognition that although the known techniques described above provide useful information about the composition of the multiphase fluids, it has been found that the known techniques do not effectively take into account changes in the linear absorption coefficient of produced and injected water mixtures having different salinities and water ion composition. Accordingly, it is an object of the invention to enhance the accuracy of multiphase fluid composition measurement techniques by taking into account changes in the linear absorption coefficient of produced and injected water mixtures having different salinities and water ion composition. It is another object of the invention to enhance the accuracy of multiphase fluid composition measurement techniques by taking into account changes in the linear absorption coefficient of produced gas and injected gas mixtures which are present, for example, in wells employing Gas-Lift methods. It is a further object of the invention to enhance the accuracy of multiphase fluid composition measurement techniques by taking into account changes in the linear absorption coefficient of produced oil and injected oil-solvent mixtures which are present, for example, in wells employing heavy oil production applications.

The above and other needs, objects and problems are addressed by the present invention, which in first aspects, provides a method and computer program product for measuring a composition of a multiphase fluid by radiating a photon beam through the multiphase fluid and measuring radiation absorption by the multiphase fluid for at least three energy levels to obtain measured radiation absorption data, providing the measured radiation absorption data to processing unit configured to calculate the composition of the multiphase fluid using the measured radiation absorption data, wherein an effect of an injected fluid on the absorption of the photon beam is taken into account during calculation of the composition of the multiphase fluid, and which includes setting up a matrix equation scheme relating a linear attenuation coefficient for the multiphase fluid to phase fractions of components in the multiphase fluid and to a volume fraction of the injected fluid, wherein the matrix equation scheme uses at least one of the following equations:

$$\mu_{oil\_prod}\alpha_{oil} + \mu_{gas\_prod}\alpha_{gas} + (\mu_{water\_prod}(1-w) + \mu_{water\_inj}w)\alpha_{water} = \mu_{mix};$$

$$\mu_{oil\_prod}\alpha_{oil} + (\mu_{gas\_prod}(1-w) + \mu_{gas\_inj}w)\alpha_{gas} + \mu_{water\_prod}\alpha_{water} = \mu_{mix}; \text{ and}$$

$$(\mu_{oil\_prod}(1-w) + \mu_{oil\_inj}w)\alpha_{oil} + \mu_{gas\_prod}\alpha_{gas} + \mu_{water\_prod}\alpha_{water} = \mu_{mix},$$

wherein the subscripts mix, water_prod, water_inj, gas_prod, gas_inj, oil_prod, and oil_inj refer to multiphase fluid, water from the aquifer, injected water, produced natural gas, injected natural gas, produced oil, and injected oil-solvent mixture, respectively, $\mu x$ is the linear attenuation coefficient of the x-component in the multiphase fluid, $\alpha x$ is the phase fraction of the x-component in the multiphase fluid, w is the volume fraction of the injected fluid in a produced fluid, and the injected fluid is one selected from a group consisting of injected water, injected natural gas, and injected oil-solvent mixture and wherein the produced fluid is one selected from a group consisting of water, gas, and oil.

In one embodiment of the first aspect, the matrix equation scheme is at least one selected from a group consisting of:

$$\begin{bmatrix} \mu_{mix}^1 \\ \mu_{mix}^2 \\ \mu_{mix}^3 \\ 1 \end{bmatrix} = \begin{bmatrix} \mu_{oil\_prod}^1 & \mu_{gas\_prod}^1 & \mu_{water\_prod}^1 & \mu_{water\_inj}^1 - \mu_{water\_prod}^1 \\ \mu_{oil\_prod}^2 & \mu_{gas\_prod}^2 & \mu_{water\_prod}^2 & \mu_{water\_inj}^2 - \mu_{water\_prod}^2 \\ \mu_{oil\_prod}^3 & \mu_{gas\_prod}^3 & \mu_{water\_prod}^3 & \mu_{water\_inj}^3 - \mu_{water\_prod}^3 \\ 1 & 1 & 1 & 0 \end{bmatrix} \begin{bmatrix} \alpha_{oil} \\ \alpha_{gas} \\ \alpha_{water} \\ w \end{bmatrix};$$

$$\begin{bmatrix} \mu_{mix}^1 \\ \mu_{mix}^2 \\ \mu_{mix}^3 \\ 1 \end{bmatrix} = \begin{bmatrix} \mu_{oil\_prod}^1 & \mu_{water\_prod}^1 & \mu_{gas\_prod}^1 & \mu_{gas\_inj}^1 - \mu_{gas\_prod}^1 \\ \mu_{oil\_prod}^2 & \mu_{water\_prod}^2 & \mu_{gas\_prod}^2 & \mu_{gas\_inj}^2 - \mu_{gas\_prod}^2 \\ \mu_{oil\_prod}^3 & \mu_{water\_prod}^3 & \mu_{gas\_prod}^3 & \mu_{gas\_inj}^3 - \mu_{gas\_prod}^3 \\ 1 & 1 & 1 & 0 \end{bmatrix} \begin{bmatrix} \alpha_{oil} \\ \alpha_{water} \\ \alpha_{gas} \\ w \end{bmatrix};$$

and $$\begin{bmatrix} \mu_{mix}^1 \\ \mu_{mix}^2 \\ \mu_{mix}^3 \\ 1 \end{bmatrix} = \begin{bmatrix} \mu_{water\_prod}^1 & \mu_{gas\_prod}^1 & \mu_{oil\_prod}^1 & \mu_{oil\_inj}^1 - \mu_{oil\_prod}^1 \\ \mu_{water\_prod}^2 & \mu_{gas\_prod}^2 & \mu_{oil\_prod}^2 & \mu_{oil\_inj}^2 - \mu_{oil\_prod}^2 \\ \mu_{water\_prod}^3 & \mu_{gas\_prod}^3 & \mu_{oil\_prod}^3 & \mu_{oil\_inj}^3 - \mu_{oil\_prod}^3 \\ 1 & 1 & 1 & 0 \end{bmatrix} \begin{bmatrix} \alpha_{water} \\ \alpha_{gas} \\ \alpha_{oil} \\ w \end{bmatrix}.$$

In another embodiment of the first aspect, w is calculated using at least one of the following equations:

$$w = \frac{Volume_{water\_inj}}{Volume_{water\_inj} + Volume_{water\_prod}};$$

$$w = \frac{Volume_{gas\_inj}}{Volume_{gas\_inj} + Volume_{gas\_prod}}; \text{ and}$$

$$w = \frac{Volume_{oil\_inj}}{Volume_{oil\_inj} + Volume_{oil\_prod}}.$$

In a further embodiment of the first aspect, the multiphase fluid is an effluent of a hydrocarbon fluid production comprising crude oil, natural gas and water, wherein a phase fraction for crude oil is in the range of 0-1, a phase fraction for natural gas is in the range of 0-1, and a phase fraction for water is in the range of 0-1.

In a second aspect, the invention provides an apparatus for measuring a composition of a multiphase fluid, including a source for radiating a photon beam through the fluid, a radiation detector measuring a level of radiation absorption by the multiphase fluid for at least three radiation energy levels, a processing unit configured to obtain measured radiation absorption data and calculate the composition of the multiphase fluid using the measured radiation absorption data, wherein the apparatus is adapted to measure the composition of the multiphase fluid in accordance with the method of the first aspect.

In one embodiment of the second aspect, the matrix equation scheme is at least one selected from a group consisting of:

$$\begin{bmatrix} \mu_{mix}^1 \\ \mu_{mix}^2 \\ \mu_{mix}^3 \\ 1 \end{bmatrix} =$$

$$\begin{bmatrix} \mu_{oil\_prod}^1 & \mu_{gas\_prod}^1 & \mu_{water\_prod}^1 & \mu_{water\_inj}^1 - \mu_{water\_prod}^1 \\ \mu_{oil\_prod}^2 & \mu_{gas\_prod}^2 & \mu_{water\_prod}^2 & \mu_{water\_inj}^2 - \mu_{water\_prod}^2 \\ \mu_{oil\_prod}^3 & \mu_{gas\_prod}^3 & \mu_{water\_prod}^3 & \mu_{water\_inj}^3 - \mu_{water\_prod}^3 \\ 1 & 1 & 1 & 0 \end{bmatrix} \begin{bmatrix} \alpha_{oil} \\ \alpha_{gas} \\ \alpha_{water} \\ w \end{bmatrix};$$

$$\begin{bmatrix} \mu_{mix}^1 \\ \mu_{mix}^2 \\ \mu_{mix}^3 \\ 1 \end{bmatrix} = \begin{bmatrix} \mu_{oil\_prod}^1 & \mu_{water\_prod}^1 & \mu_{gas\_prod}^1 & \mu_{gas\_inj}^1 - \mu_{gas\_prod}^1 \\ \mu_{oil\_prod}^2 & \mu_{water\_prod}^2 & \mu_{gas\_prod}^2 & \mu_{gas\_inj}^2 - \mu_{gas\_prod}^2 \\ \mu_{oil\_prod}^3 & \mu_{water\_prod}^3 & \mu_{gas\_prod}^3 & \mu_{gas\_inj}^3 - \mu_{gas\_prod}^3 \\ 1 & 1 & 1 & 0 \end{bmatrix} \begin{bmatrix} \alpha_{oil} \\ \alpha_{water} \\ \alpha_{gas} \\ w \end{bmatrix};$$

and $$\begin{bmatrix} \mu_{mix}^1 \\ \mu_{mix}^2 \\ \mu_{mix}^3 \\ 1 \end{bmatrix} = \begin{bmatrix} \mu_{water\_prod}^1 & \mu_{gas\_prod}^1 & \mu_{oil\_prod}^1 & \mu_{oil\_inj}^1 - \mu_{oil\_prod}^1 \\ \mu_{water\_prod}^2 & \mu_{gas\_prod}^2 & \mu_{oil\_prod}^2 & \mu_{oil\_inj}^2 - \mu_{oil\_prod}^2 \\ \mu_{water\_prod}^3 & \mu_{gas\_prod}^3 & \mu_{oil\_prod}^3 & \mu_{oil\_inj}^3 - \mu_{oil\_prod}^3 \\ 1 & 1 & 1 & 0 \end{bmatrix} \begin{bmatrix} \alpha_{water} \\ \alpha_{gas} \\ \alpha_{oil} \\ w \end{bmatrix}.$$

In another embodiment of the second aspect, w is calculated using at least one of the following equations:

$$w = \frac{Volume_{water\_inj}}{Volume_{water\_inj} + Volume_{water\_prod}};$$

$$w = \frac{Volume_{gas\_inj}}{Volume_{gas\_inj} + Volume_{gas\_prod}}; \text{ and}$$

$$w = \frac{Volume_{oil\_inj}}{Volume_{oil\_inj} + Volume_{oil\_prod}}.$$

In a further embodiment of the second aspect, the source for radiating the photon beam includes at least one selected from a group consisting of an x-ray source and a γ-ray source.

In a still further embodiment of the second aspect, the multiphase fluid is an effluent of a hydrocarbon fluid production including crude oil, natural gas and water, wherein a phase fraction for crude oil is in the range of 0-1, a phase fraction for natural gas is in the range of 0-1, and a phase fraction for water is in the range of 0-1.

Advantageously, the novel method, apparatus and computer program product can be used for measuring the composition of the multiphase fluid produced by one or more crude oil production wells where the crude oil is usually accompanied by varying quantities of natural gas and/or water. Such a measurement provides information on the composition of the multiphase fluid (e.g., phase fraction of oil, phase fraction of natural gas, and phase fraction of water) in the pipeline from each well. The information on the composition of the multiphase fluid in turn can be used to monitor and/or optimize the production of a crude oil reservoir.

Still other aspects, features, and advantages of the present invention are readily apparent from the entire description thereof, including the figures, which illustrate a number of exemplary embodiments and implementations. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which.

DETAILED DESCRIPTION

Figure 1:
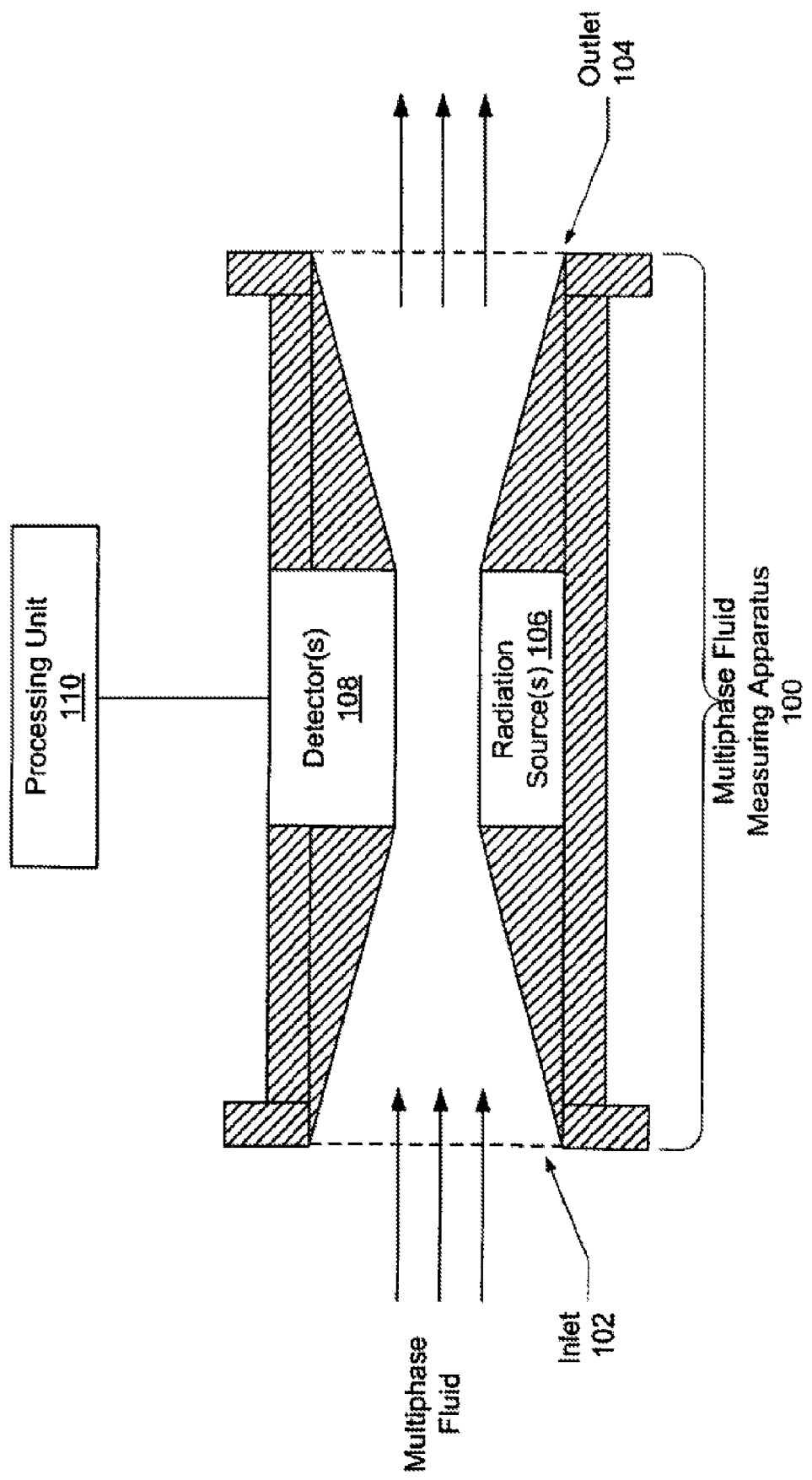
FIG. 1 shows a multiphase fluid measuring apparatus in accordance with one or more embodiments of the invention.

Various embodiments and aspects of the invention will now be described in detail with reference to the accompanying figures. The terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited. Exemplary embodiments of the invention will now be described in detail with reference to the accompanying figures, in which like elements may be denoted by like reference numerals for consistency.

Exemplary embodiments of the invention will now be described in detail with reference to the accompanying figures. Like items in the figures are denoted with like reference numerals for consistency.

In embodiments of the invention, numerous specific details are set forth in order to provide a more thorough understanding of the invention. However, it will be apparent to one of ordinary skill in the art that the invention can be practiced without these specific details. In other instances, well-known features have not been described in detail to avoid unnecessarily complicating the description.

In general, embodiments of the invention relate to a method and apparatus for measuring the composition of a multiphase fluid. More specifically, embodiments of the invention relate to a method and apparatus for determining the phase fraction for each component (e.g., natural gas, oil, water, etc.) in the multiphase fluid.

FIG. 1 shows a multiphase fluid measuring apparatus 100 in accordance with one or more embodiments of the invention. The multiphase fluid measuring apparatus 100 includes an inlet 102 from which the multiphase fluid enters and an outlet 104 from which the multiphase fluid exits. Further, the multiphase fluid measuring apparatus 100 includes a conduit, bounded by the inlet 102 and the outlet 104, through which the multiphase fluid passes. In addition, the multiphase fluid measuring apparatus 100 includes one or more radiation sources 106 and one or more detectors 108.

In one embodiment of the invention, the multiphase fluid is a liquid that includes more than one phase, such as water-based or oil-based liquids, solid material, or natural gas. The multiphase fluid may flow in accordance with one or more of the following flow regimes: bubble flow (e.g., continuous liquid phase with evenly dispersed gas bubbles), slug flow (e.g., continuous liquid phase with irregular gas bubbles), transition flow (e.g., interrupted liquid phase with chaotic gas distribution), and mist flow (e.g., continuous gas phase with liquid entrained as mist and an annular film on tubing wall).

The multiphase fluid measuring apparatus 100 can be constructed out of any material suitable for transmitting the multiphase fluid and for housing the radiation source(s) 106 and the detector(s) 108. For example, the multiphase fluid measuring apparatus 100 can be constructed using ceramic, a carbon fiber reinforced epoxy, any other suitable material, and/or any combination thereof.

In one embodiment of the invention, the radiation source(s) 106 corresponds to one or more radioactive materials and/or devices, which emit x-rays and/or γ-rays. The radiation source(s) 106 are selected such that suitable energy levels (e.g., e1, e2, and e3) are emitted in order to obtain the linear attenuation coefficient of the multiphase fluid (e.g., $\mu_{mix}^i$, where i=e1 ... e3). For example, x-rays can be generated using an x-ray tube and γ-rays can be generated using a chemical radioactive source (e.g., Barium 133, Americium 241, etc).

In one embodiment of the invention, the detector(s) 108 is configured to detect radiation emitted from the radiation source(s) 106. The multiphase fluid measuring apparatus 100 can include one or more source(s) and detector(s) 108. Further, the source(s) and detector(s) 108 can be circumferentially spaced around the circumference of the conduit. By using multiple source(s) and detectors 108, a determination can be made about the homogeneity of the multiphase fluid by comparing the phase fraction for each of the components (e.g., oil, natural gas, water) calculated using data related to the detected radiation obtained at each of the source(s) 106 and detector(s) 108. Alternatively, the data related to the detected radiation obtained at each of the detectors 108 can be averaged on a per-energy level basis and the resulting data used to calculate the phase fraction for each of the components.

In one embodiment of the invention, the data related to the detected radiation obtained at each of the detector(s) 108 is transmitted to a processing unit 110. The processing unit 110 can be housed within the multiphase fluid measuring apparatus 100 or can be located outside of the multiphase fluid measuring apparatus 100. In one embodiment of the invention, the processing unit 110 is configured to calculate the phase fraction for each of the components (e.g., $\alpha_{oil}$, $\alpha_{gas}$, $\alpha_{water}$) in the multiphase fluid. In addition, the processing unit 110 is configured to calculate the volume fraction of the injected fluid (w). The method used by the processing unit to calculate $\alpha_{oil}$, $\alpha_{gas}$, $\alpha_{water}$, and w is described below.

Figure 2:
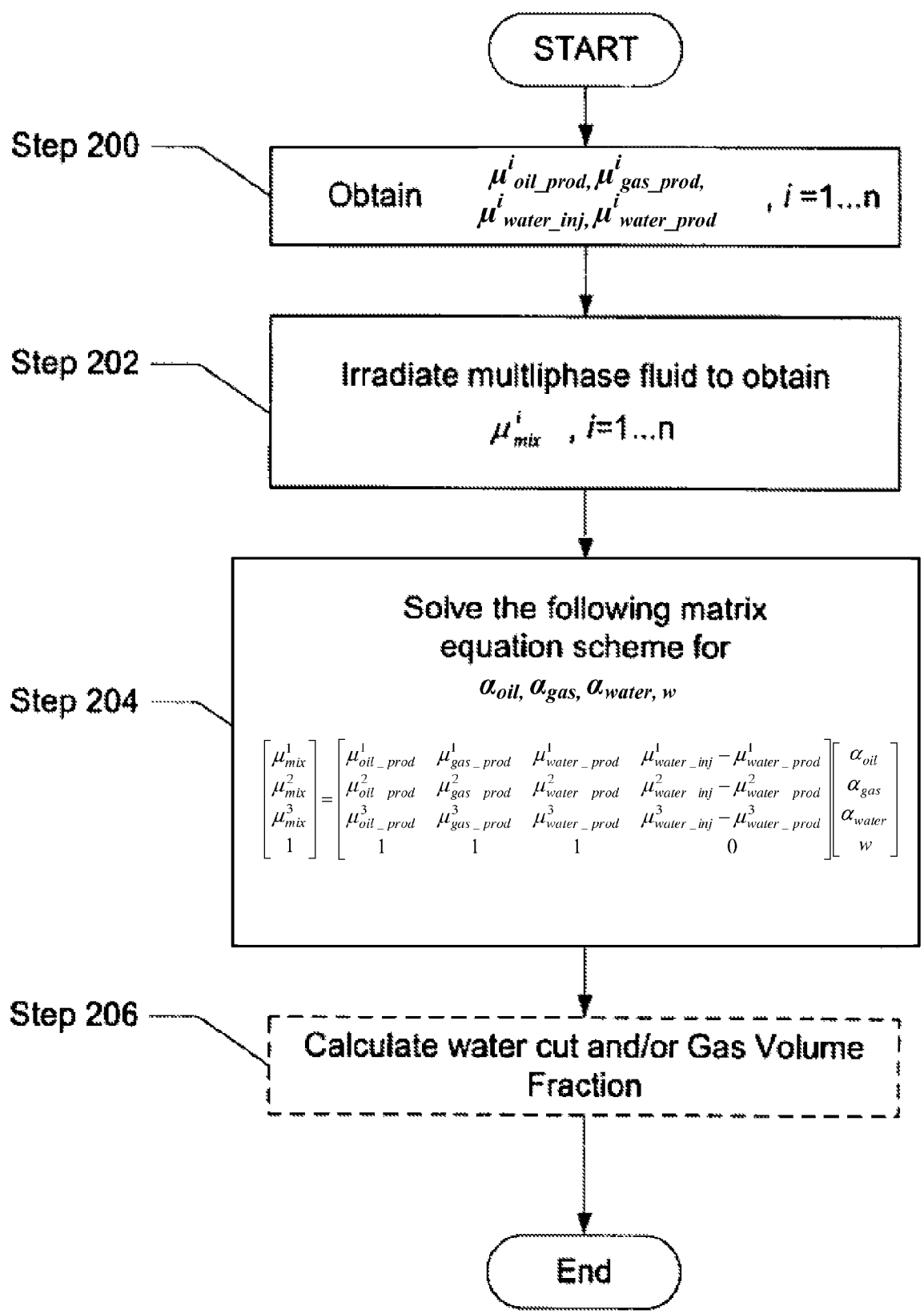
FIG. 2 shows a flowchart in accordance with one or more embodiments of the invention.

FIG. 2 shows a flowchart in accordance with one or more embodiments of the invention. In one or more embodiments, one or more of the steps shown in FIG. 2 can be omitted, repeated, and/or performed in a different order than that shown in FIG. 2. Accordingly, the specific arrangement of steps shown in FIG. 2 should not be construed as limiting the scope of the invention.

In Step 200, $\mu_{oil\_prod}^i$, $\mu_{gas\_prod}^i$, $\mu_{water\_inj}^i$, $\mu_{water\_prod}^i$, are obtained, where i=energy levels e1 . . . e3 denoted as 1 . . . n (e.g., 1 . . . 3). In one embodiment of the invention, $\mu_{oil\_prod}^i$ corresponds to the linear attenuation coefficient of oil, $\mu_{gas\_prod}^i$ corresponds to the linear attenuation coefficient of natural gas, $\mu_{water\_inj}^i$ corresponds to the linear attenuation coefficient of water injected into a well (reservoir formation) (e.g., the well (reservoir) from which the multiphase fluid was obtained), and $\mu_{water\_prod}^i$ corresponds to the linear attenuation coefficient of water from the aquifer (e.g., ground water obtained from the aquifer located proximate to the well).

In one embodiment of the invention, the aforementioned linear attenuation coefficients can be obtained by measuring the radiation absorption of pure samples of oil, natural gas, injected water, and water from the aquifer using the apparatus described in FIG. 1. In one embodiment of the invention, $\mu_{oil\_prod}^i$, $\mu_{gas\_prod}^i$, $\mu_{water\_inj}^i$, and $\mu_{water\_prod}^i$ can be obtained by using the following equation:

$$\frac{I}{I_0} = e^{-\mu x},$$

where I is the radiation detected by a detector, $I_0$ is the radiation emitted from a radiation source, $\mu$ is the linear attenuation coefficient, and x is the distance the radiation travels through the fluid to reach the detector (e.g., ≈diameter of the conduit). Once the mass attenuation coefficient is obtained, the density of the fluid ($\rho$) (e.g., density of oil, natural gas, injected water, and water from the aquifer) can be used to obtain the linear attenuation coefficient ($\mu$) for the fluid.

In one embodiment of the invention, if the mass attenuation coefficients for the injected water and water from the aquifer are not available, the following method can be used to determine the aforementioned mass attenuation coefficients. Initially, the mass attenuation coefficients ($\nu$) for brine (e.g., water saturated with salt at a particular temperature) and salt (e.g., salt present in the water from which the mass attenuation coefficient is to be determined, e.g., salt in injected water or salt in water from aquifer) at three energy levels (e.g., e1, e2, and e3) are obtained.

Using the aforementioned mass attenuation coefficients, the following equation is solved for the mass attenuation coefficient of water, where the "water" corresponds to one of injected water and aquifer water:

$$\nu_{brine}^i = \nu_{water}^i + \sigma \sum_{ions} C_{ion}(\nu_{ion}^i - \nu_{water}^i),$$

where $\sigma$ is the mass fraction of the salts in the water (mass %) and $C_{ion}$ is the portion of a particular ion-salt in the salt (dimensionless units). $\mu_{water}^i$ is then calculated using the following equation:

$$u_{water}^i = \nu_{water}^i \rho(\sigma),$$

where $\rho(\sigma)$ corresponds to the density of water for the given mass fraction of salts in the water. In one embodiment of the invention, $\rho(\sigma)$ for the water is measured using the appropriate equipment. Alternatively, in one embodiment of the invention, $\rho(\sigma)$ is calculated using the following linear approximation: $\rho(\sigma) = \rho_0 + \rho_1 \sigma$, wherein $\rho_0$ is the density of pure water at a given temperature and $\rho_1$ is the water density first expansion coefficient at the given temperature. Alternatively, in one embodiment of the invention, the density of water can be obtained by taking the Taylor series of $\rho(\sigma)$. The above method can be used to obtain the linear attenuation coefficient of the injected water and/or the water from the aquifer.

Returning to FIG. 2, at Step 202, the multiphase fluid is irradiated to obtain $\mu_{mix}^i$, where i=1 . . . 3. Those skilled in the art will appreciate that the multiphase fluid can be irradiated at more than three energy levels.

In Step 204, the data obtained in steps 200 and 202, is used to solve the following matrix equation scheme to obtain $\alpha_{oil}$, $\alpha_{gas}$, $\alpha_{water}$ and w:

$$\begin{bmatrix} \mu_{mix}^1 \\ \mu_{mix}^2 \\ \mu_{mix}^3 \\ 1 \end{bmatrix} = \begin{bmatrix} \mu_{oil\_prod}^1 & \mu_{gas\_prod}^1 & \mu_{water\_prod}^1 & \mu_{water\_inj}^1 - \mu_{water\_prod}^1 \\ \mu_{oil\_prod}^2 & \mu_{gas\_prod}^2 & \mu_{water\_prod}^2 & \mu_{water\_inj}^2 - \mu_{water\_prod}^2 \\ \mu_{oil\_prod}^3 & \mu_{gas\_prod}^3 & \mu_{water\_prod}^3 & \mu_{water\_inj}^3 - \mu_{water\_prod}^3 \\ 1 & 1 & 1 & 0 \end{bmatrix} \begin{bmatrix} \alpha_{oil} \\ \alpha_{gas} \\ \alpha_{water} \\ w \end{bmatrix}$$

The above matrix equation scheme is derived from the following equations:

$$\alpha_{oil} + \alpha_{gas} + \alpha_{water} = 1$$

$$\mu_{oil\_prod}\alpha_{oil} + \mu_{gas\_prod}\alpha_{gas} + (\mu_{water\_prod}(1-w) + \mu_{water\_inj}w)\alpha_{water} = \mu_{mix} \ (i=1\ldots 3),$$

where $\mu_x$ is the linear attenuation coefficient of the x-component (e.g., oil, natural gas, injected water, water from the aquifer) in the multiphase fluid, $\alpha_x$ is the phase fraction of the x-component (e.g., oil, natural gas, water) in the multiphase fluid, w is the volume fraction of the injected fluid in a produced fluid and is defined using the following formula:

$$w = \frac{Volume_{water\_inj}}{Volume_{water\_inj} + Volume_{water\_prod}},$$

where $Volume_{water\_inj}$ is the volume of the injected water and $volume_{water\_prod}$ is the volume of the water from the aquifer.

By introducing the term w, the above matrix equation scheme is able to take into account the effects of the ion compositions in the injected water and the water from the aquifer. Further, the above matrix equation scheme takes into account the effect of the actual ions in the injected water and water from the aquifer as opposed to relying on a NaCl-equivalent for the ions. By introducing w, the above matrix equation scheme is able to take into account the different absorption cross section areas of the different ions present in the water (injected water and water from the aquifer), which have an impact on the linear attenuation coefficients used to determine the phase fractions of the components in the multiphase fluid (e.g., $\alpha_{oil}$, $\alpha_{gas}$, $\alpha_{water}$). The above approach enables more accurate mass and/or linear attenuation coefficients to be used in the calculation of the phase fractions of the components in the multiphase fluid (e.g., $\alpha_{oil}$, $\alpha_{gas}$, $\alpha_{water}$), which results in more accurate phase fractions.

Continuing with the discussion of FIG. 2, once the matrix equation scheme in Step 204 has been solved, one or more of the following values $\alpha_{oil}$, $\alpha_{gas}$, $\alpha_{water}$, and w can be used to optionally calculate Water Liquid Ratio (WLR) and/or Gas Volume Fraction (Step 206).

Water cut is $$WLR = \frac{\alpha_{water}}{\alpha_{water} + \alpha_{oil}},$$

gas volume fraction GVF=$\alpha_{gas}$ or the predictable function of $\alpha_{gas}$ and gas/liquid properties, if the slip between gas and liquid is taken into account.

In one embodiment of the invention, the processing unit 100 is configured to obtain the information described in Step 200 from a database and/or other information source. Alternatively, the processing unit 100 may, in the absence of a source of from which to obtain the information described in Step 200, can be configured to calculate (or otherwise determine) the one or more pieces of information described in Step 200.

In one embodiment of the invention, if the processing unit 110 is housed within the multiphase fluid measuring apparatus 100 (or is otherwise controlling the operation of the multiphase fluid measuring apparatus 100), and the processing unit 110 is configured to control the multiphase fluid measuring apparatus 100 in order to obtain the mass attenuation coefficient and/or the linear attenuation coefficient of the multiphase fluid for at least three energy levels. If the processing unit 110 is not housed within the multiphase fluid measuring apparatus 100 (or is otherwise not controlling the operation of the multiphase fluid measuring apparatus 100, then the processing unit 110 is configured to receive the mass attenuation coefficient and/or obtain the linear attenuation coefficient of the multiphase fluid for at least three energy levels from the multiphase fluid measuring apparatus 100.

In one embodiment of the invention, the processing unit 110 is configured to perform the Step 204. In one embodiment of the invention, the processing unit 110 can be configured to perform Step 206. Alternatively, the processing unit 110 can be configured to send the results of Step 204 to another system(s) (not shown) that is configured to perform Step 206.

Figure 3A:
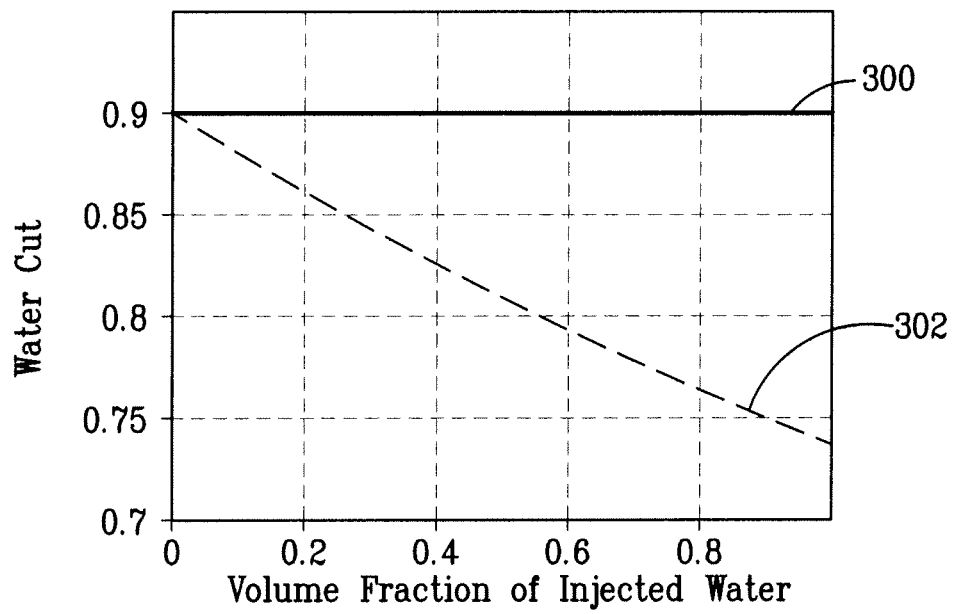
FIGS. 3A, 3B, and 4 show results of using one or more embodiments of the invention.
Figure 3B:
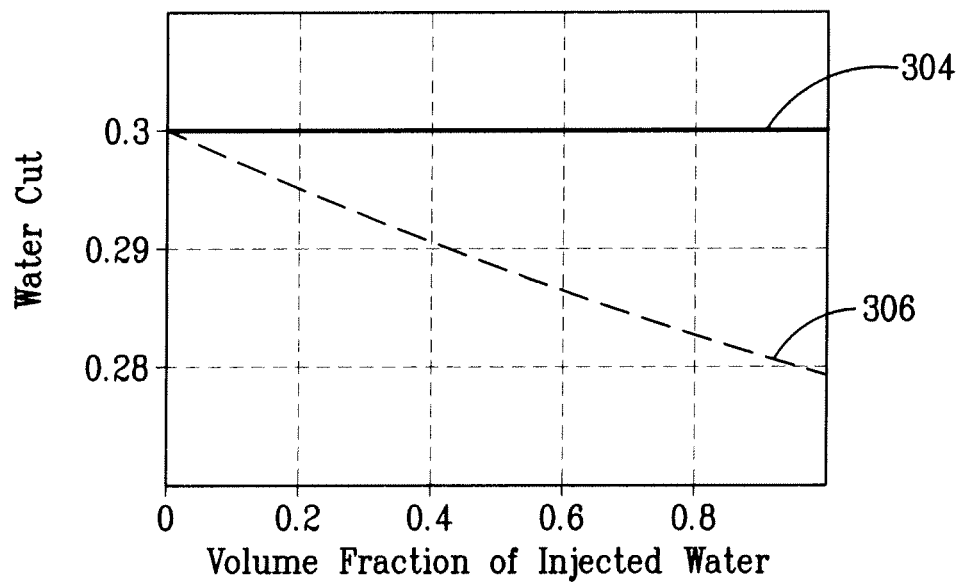
Figure 4:
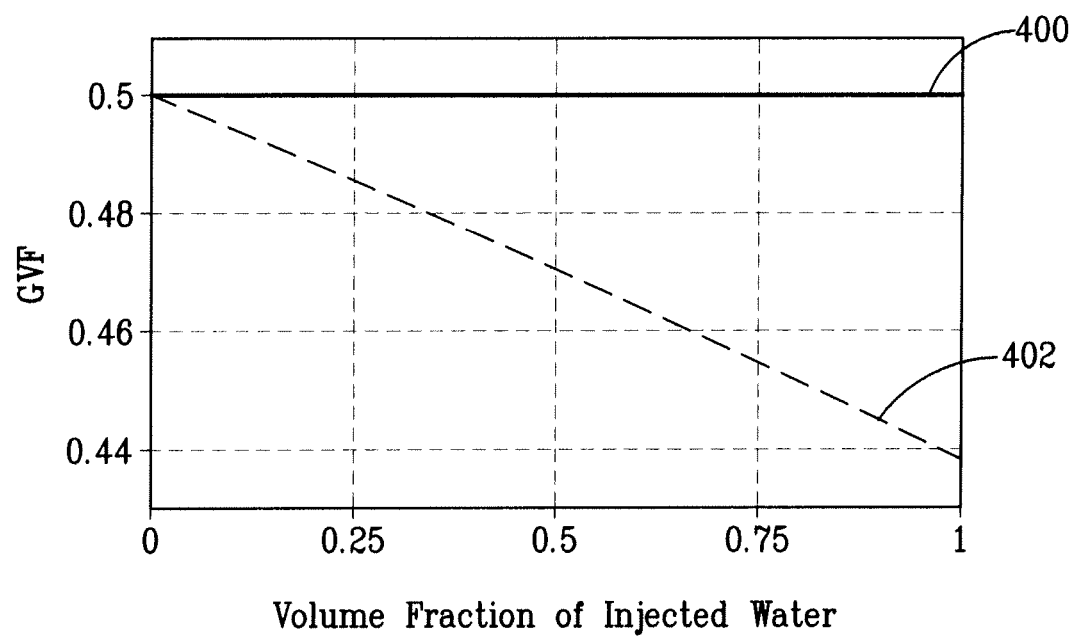

FIGS. 3A, 3B, and 4 show results of using one or more embodiments of the invention. More specifically, the following figures compare the method of the present invention with the method described in European Patent No. 0 896 666.

The following results shown in FIGS. 3A, 3B, and 4 were obtained by calculating the water cut and GVF for different values of w (e.g., the volume fraction of the injected water). The salt composition of the injected water and water from the aquifer used for the comparison is shown in Table 1.

TABLE 1

Salt Sets for Comparison

| Ions | Salt composition, [g/l] | |
|---|---|---|
| | Injected water | Water from aquifer |
| Na+ | 3.243 | 55.0 |
| K+ | 0 | 0.22 |
| Ca+2 | 0.8 | 43.19 |
| Cl− | 5.556 | 181.78 |
| SO4−2 | 0 | 0.165 |
| Mg+2 | 0.1 | 4.82 |
| HCO3− | 0.153 | 0.118 |
| Total Dissolved | 9.856 | 285.293 |

FIG. 3A shows the results of using the method of the present invention as compared with the method described in European Patent No. 0 896 666 to determine water cut, where the water cut in the multiphase fluid is 0.9 and GVF is 0.4. As shown in FIG. 3A, when water cut is calculated using $\alpha_{oil}$, $\alpha_{gas}$, and $\alpha_{water}$ obtained using one or more embodiments of the present invention, the increase in volume fraction of injected water does not affect the resulting water cut (see Curve 300 in FIG. 3A). In contrast, as the volume of injected water increases, the accuracy of the calculated water cut using $\alpha_{oil}$, $\alpha_{gas}$, and $\alpha_{water}$ obtained using the method described in European Patent No. 0 896 666 decreases (see Curve 302 in FIG. 3A).

FIG. 3B shows the results of using the method of the present invention as compared with the method described in European Patent No. 0 896 666 to determine water cut, where water cut in the multiphase fluid is 0.3 and GVF is 0.8. As shown in FIG. 3A, when water cut is calculated using $\alpha_{oil}$, $\alpha_{gas}$, and $\alpha_{water}$ obtained using one or more embodiments of the present invention, the increase in volume fraction of injected water does not affect the resulting water cut (see Curve 304 in FIG. 3B). In contrast, as the volume of injected water increases, the accuracy of the calculated water cut using $\alpha_{oil}$, $\alpha_{gas}$, and $\alpha_{water}$ obtained using the method described in European Patent No. 0 896 666 decreases (see Curve 306 in FIG. 3B).

FIG. 4 shows the results of using the method of the present invention as compared with the method described in European Patent No. 0 896 666 to determine GVF, where water cut in the multiphase fluid is 0.5 and GVF is 0.5. As shown in FIG. 3A, when GVF is calculated using $\alpha_{oil}$, $\alpha_{gas}$, and $\alpha_{water}$ obtained using one or more embodiments of the present invention, the increase in volume fraction of injected water does not affect the resulting GVF (see Curve 400 in FIG. 4). In contrast, as the volume of injected water increases, the accuracy of the calculated water cut using $\alpha_{oil}$, $\alpha_{gas}$, and $\alpha_{water}$ obtained using the method described in European Patent No. 0 896 666 decreases (see Curve 402 in FIG. 4).

In one embodiment of the invention, the above matrix scheme can be modified to take into account the variations in the linear attenuation coefficient of produced natural gas and injected natural gas, when a Gas-Lift method is used for well-bore exploitation. In such embodiments, the following matrix equation scheme can be used:

$$\begin{bmatrix} \mu_{mix}^1 \\ \mu_{mix}^2 \\ \mu_{mix}^3 \\ 1 \end{bmatrix} = \begin{bmatrix} \mu_{oil\_prod}^1 & \mu_{water\_prod}^1 & \mu_{gas\_prod}^1 & \mu_{gas\_inj}^1 - \mu_{gas\_prod}^1 \\ \mu_{oil\_prod}^2 & \mu_{water\_prod}^2 & \mu_{gas\_prod}^2 & \mu_{gas\_inj}^2 - \mu_{gas\_prod}^2 \\ \mu_{oil\_prod}^3 & \mu_{water\_prod}^3 & \mu_{gas\_prod}^3 & \mu_{gas\_inj}^3 - \mu_{gas\_prod}^3 \\ 1 & 1 & 1 & 0 \end{bmatrix} \begin{bmatrix} \alpha_{oil} \\ \alpha_{water} \\ \alpha_{gas} \\ w \end{bmatrix}$$

The above matrix equation scheme is derived from the following equations:

$$\alpha_{oil} + \alpha_{gas} + \alpha_{water} = 1$$

$$\mu_{oil\_prod}\alpha_{oil} + (\mu_{gas\_prod}(1-w) + \mu_{gas\_inj}w)\alpha_{gas} + \mu_{water\_prod}\alpha_{water} = \mu_{mix}^i \ (i=1\ldots3),$$

where $\mu_x$ is the linear attenuation coefficient of the x-component (e.g., oil, produced natural gas, injected natural gas, water) in the multiphase fluid, $\alpha_x$ is the phase fraction of the x-component in the multiphase fluid, w is the volume fraction of the injected fluid in a produced fluid and is defined using the following formula:

$$w = \frac{Volume_{gas\_inj}}{Volume_{gas\_inj} + Volume_{gas\_prod}},$$

where $Volume_{gas\_inj}$ is the volume of the injected gas and $Volume_{gas\_prod}$ is the volume of produced gas.

In one embodiment of the invention, the above matrix scheme can be modified to take into account the variations in the linear attenuation coefficient of oil and injected oil-solvent mixtures, when the multiphase fluid is produced as a result of a heavy oil production application. In such embodiments, the following matrix equation scheme can be used:

$$\begin{bmatrix} \mu_{mix}^1 \\ \mu_{mix}^2 \\ \mu_{mix}^3 \\ 1 \end{bmatrix} = \begin{bmatrix} \mu_{water\_prod}^1 & \mu_{gas\_prod}^1 & \mu_{oil\_prod}^1 & \mu_{oil\_inj}^1 - \mu_{oil\_prod}^1 \\ \mu_{water\_prod}^2 & \mu_{gas\_prod}^2 & \mu_{oil\_prod}^2 & \mu_{oil\_inj}^2 - \mu_{oil\_prod}^2 \\ \mu_{water\_prod}^3 & \mu_{gas\_prod}^3 & \mu_{oil\_prod}^3 & \mu_{oil\_inj}^3 - \mu_{oil\_prod}^3 \\ 1 & 1 & 1 & 0 \end{bmatrix} \begin{bmatrix} \alpha_{water} \\ \alpha_{gas} \\ \alpha_{oil} \\ w \end{bmatrix}$$

The above matrix equation scheme is derived from the following equations:

$$\alpha_{oil} + \alpha_{gas} + \alpha_{water} = 1$$

$$(\mu_{oil\_prod}(1-w) + \mu_{oil\_inj} w)\alpha_{oil} + \mu_{gas\_prod}\alpha_{gas} + \mu_{water\_prod}\alpha_{water} = \mu_{mix}^i, (i=1 \ldots 3),$$

where $\mu_x$ is the linear attenuation coefficient of the x-component (e.g., oil, gas, produced oil, injected oil-solvent mixtures, water) in the multiphase fluid, $\alpha_x$ is the phase fraction of the x-component in the multiphase fluid, w is the volume fraction of the injected fluid in a produced fluid and is defined using the following formula:

$$w = \frac{Volume_{oil\_inj}}{Volume_{oil\_inj} + Volume_{oil\_prod}},$$

where $Volume_{oil\_inj}$ is the volume of the oil-solvent mixture and $Volume_{oil\_prod}$ is the volume of produced oil.

In one embodiment of the invention, a single multiphase fluid measuring apparatus 100 can be configured to determine, and w using any of the above matrix equation schemes.

Figure 5:
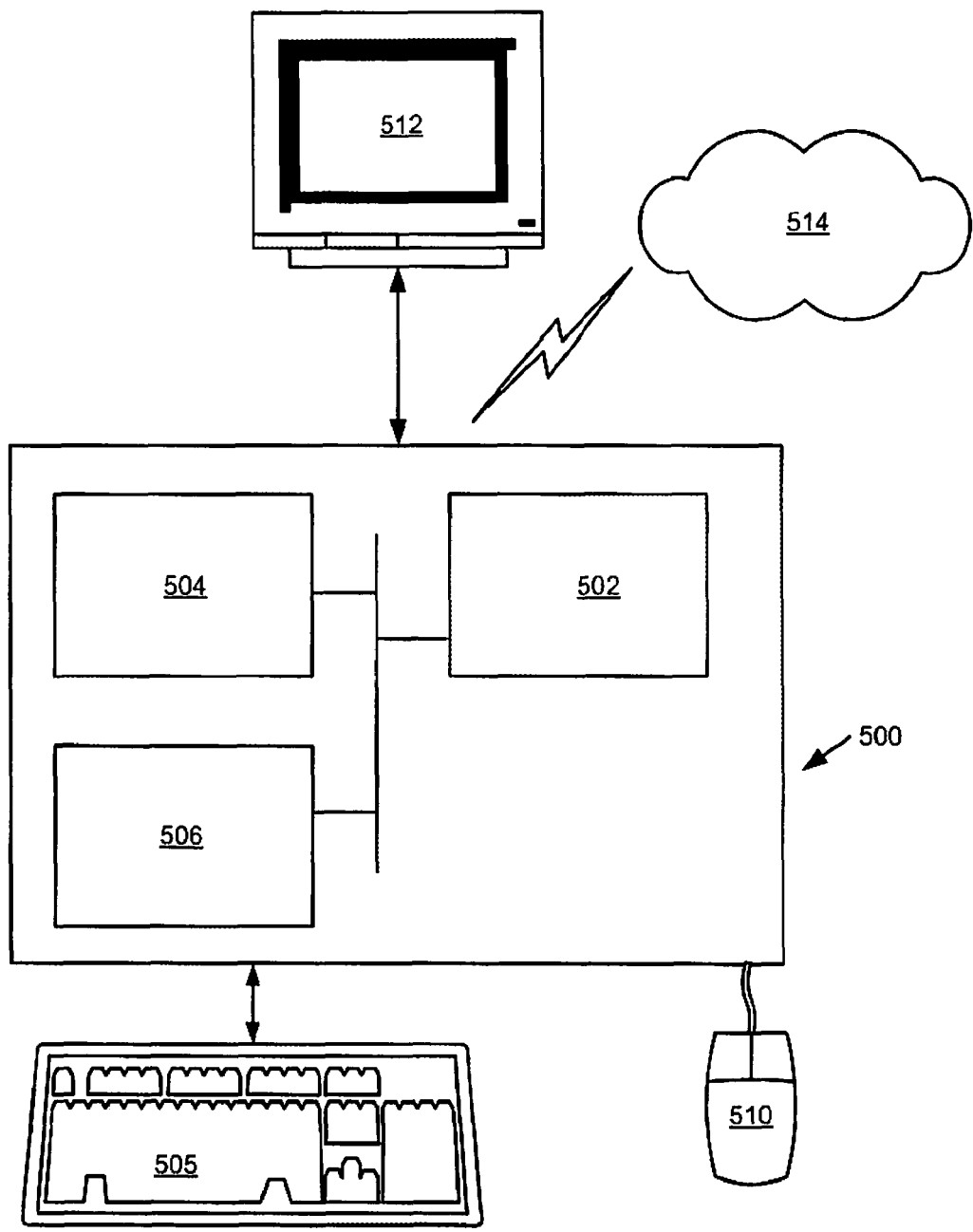
FIG. 5 shows a computer system in accordance with one or more embodiments of the invention.

In one embodiment of the invention, the processing unit 110 includes the functionality of the computer system described in FIG. 5. As shown in FIG. 5, a computer system 500 includes a processor 502, associated memory 504, a storage device 506, and numerous other elements and functionalities typical of today's computers (not shown). The computer 500 can also include input means, such as a keyboard 508 and a mouse 510, and output means, such as a monitor 512. The computer system 500 is connected to a local area network (LAN) or a wide area network (e.g., the Internet) (not shown) via a network interface connection 514. Those skilled in the art will appreciate that these input and output means may take other forms, now known or later developed.

Further, those skilled in the art will appreciate that one or more elements of the aforementioned computer system 500 can be located at a remote location and connected to the other elements over a network. Further, the invention can be implemented on a distributed system having a plurality of nodes, where each portion of the invention can be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention can be stored on a computer readable medium such as a compact disc (CD), a diskette, a tape, a file, or any other computer readable storage device.

Thus, the above-described devices and subsystems of the exemplary embodiments of FIGS. 1-5 can include, for example, any suitable servers, workstations, personal computers (PCs), laptop computers, personal digital assistants (PDAs), Internet appliances, handheld devices, cellular telephones, wireless devices, other electronic devices, and the like, capable of performing the processes of the exemplary embodiments of FIGS. 1-5. The devices and subsystems of the exemplary embodiments of FIGS. 1-5 can communicate with each other using any suitable protocol and can be implemented using one or more programmed computer systems or devices.

One or more interface mechanisms can be used with the exemplary embodiments of FIGS. 1-5, including, for example, Internet access, telecommunications in any suitable form (e.g., voice, modem, and the like), wireless communications media, and the like. For example, the employed communications networks can include one or more wireless communications networks, cellular communications networks, 3 G communications networks, Public Switched Telephone Network (PSTNs), Packet Data Networks (PDNs), the Internet, intranets, a combination thereof, and the like. Accordingly, the devices and subsystems of the exemplary embodiments of FIGS. 1-5 can be implemented on the World Wide Web.

It is to be understood that the devices and subsystems of the exemplary embodiments of FIGS. 1-5 are for exemplary purposes, as many variations of the specific hardware and/or software used to implement the exemplary embodiments are possible, as will be appreciated by those skilled in the relevant art(s). For example, the functionality of one or more of the devices and subsystems of the exemplary embodiments of FIGS. 1-5 can be implemented via one or more programmed computer systems or devices.

To implement such variations as well as other variations, a single computer system can be programmed to perform the special purpose functions of one or more of the devices and subsystems of the exemplary embodiments of FIGS. 1-5. On the other hand, two or more programmed computer systems or devices can be substituted for any one of the devices and subsystems of the exemplary embodiments of FIGS. 1-5. Accordingly, principles and advantages of distributed processing, such as redundancy, replication, and the like, also can be implemented, as desired, to increase the robustness and performance the devices and subsystems of the exemplary embodiments of FIGS. 1-5.

The devices and subsystems of the exemplary embodiments of FIGS. 1-5 can store information relating to various processes described herein. This information can be stored in one or more memories, such as a hard disk, optical disk, magneto-optical disk, RAM, and the like, of the devices and subsystems of the exemplary embodiments of FIGS. 1-5. One or more databases of the devices and subsystems of the exemplary embodiments of FIGS. 1-5 can store the information used to implement the exemplary embodiments of the present invention. The databases can be organized using data structures (e.g., records, tables, arrays, fields, graphs, trees, lists, and the like) included in one or more memories or storage devices listed herein. The processes described with respect to the exemplary embodiments of FIGS. 1-5 can include appropriate data structures for storing data collected and/or generated by the processes of the devices and subsystems of the exemplary embodiments of FIGS. 1-5 in one or more databases thereof.

All or a portion of the devices and subsystems of the exemplary embodiments of FIGS. 1-5 can be conveniently implemented using one or more general purpose computer systems, microprocessors, digital signal processors, microcontrollers, and the like, programmed according to the teachings of the exemplary embodiments of the present invention, as will be appreciated by those skilled in the computer and software arts. Appropriate software can be readily prepared by programmers of ordinary skill based on the teachings of the exemplary embodiments, as will be appreciated by those skilled in the software art. In addition, the devices and subsystems of the exemplary embodiments of FIGS. 1-5 can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware circuitry and/or software.

Stored on any one or on a combination of computer readable media, the exemplary embodiments of the present invention can include software for controlling the devices and subsystems of the exemplary embodiments of FIGS. 1-5, for driving the devices and subsystems of the exemplary embodiments of FIGS. 1-5, for enabling the devices and subsystems of the exemplary embodiments of FIGS. 1-5 to interact with a human user, and the like. Such software can include, but is not limited to, device drivers, firmware, operating systems, development tools, applications software, and the like. Such computer readable media further can include the computer program product of an embodiment of the present invention for performing all or a portion (if processing is distributed) of the processing performed in implementing the exemplary embodiments of FIGS. 1-5. Computer code devices of the exemplary embodiments of the present invention can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary embodiments of the present invention can be distributed for better performance, reliability, cost, and the like.

As stated above, the devices and subsystems of the exemplary embodiments of FIGS. 1-5 can include computer readable medium or memories for holding instructions programmed according to the teachings of the present invention and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave, or any other suitable medium from which a computer can read.

While the present inventions have been described in connection with a number of exemplary embodiments, and implementations, the present inventions are not so limited, but rather cover various modifications, and equivalent arrangements, which fall within the purview of the appended claims.

The invention claimed is:

1. A method for measuring a composition of a multiphase fluid, the method comprising:
   radiating a photon beam through the multiphase fluid;
   measuring radiation absorption by the multiphase fluid for at least three energy levels to obtain measured radiation absorption data;
   providing the measured radiation absorption data to processing unit configured to calculate the composition of the multiphase fluid using the measured radiation absorption data, wherein an effect of an injected fluid on the absorption of the photon beam is taken into account during calculation of the composition of the multiphase fluid;
   setting up a matrix equation scheme relating a linear attenuation coefficient for the multiphase fluid to phase fractions of components in the multiphase fluid and to a volume fraction of the injected fluid, wherein the matrix equation scheme uses at least one the following equations:

$$\mu_{oil\_prod}\alpha_{oil} + \mu_{gas\_prod}\alpha_{gas} + (\mu_{water\_prod}(1-w) + \mu_{water\_inj}w)\alpha_{water} = \mu_{mix};$$

$$\mu_{oil\_prod}\alpha_{oil} + (\mu_{gas\_prod}(1-w) + \mu_{gas\_inj}w)\alpha_{gas} + \mu_{water\_prod}\alpha_{water} = \mu_{mix}; \text{ and}$$

$$(\mu_{oil\_prod}(1-w) + \mu_{oil\_inj}w)\alpha_{oil} + \mu_{gas\_prod}\alpha_{gas} + \mu_{water\_prod}\alpha_{water} = \mu_{mix},$$

wherein the subscripts mix, water_prod, water_inj, gas_prod, gas_inj, oil_prod, and oil_inj refer to multiphase fluid, water from the aquifer, injected water, produced natural gas, injected natural gas, produced oil, and injected oil-solvent mixture, respectively, $\mu x$ is the linear attenuation coefficient of the x-component in the multiphase fluid, $\alpha x$ is the phase fraction of the x-component in the multiphase fluid, and w is the volume fraction of the injected fluid in a produced fluid, wherein the injected fluid is one selected from a group consisting of injected water, injected natural gas, and injected oil-solvent mixture, and the produced fluid is one selected from a group consisting of water, gas, and oil; and
   calculating the composition of the multiphase fluid with the processing unit using the measured radiation absorption data and the matrix equation scheme.

2. The method of claim 1, wherein the matrix equation scheme is at least one selected from a group consisting of:

$$\begin{bmatrix} \mu_{mix}^1 \\ \mu_{mix}^2 \\ \mu_{mix}^3 \\ 1 \end{bmatrix} =$$

-continued $$\begin{bmatrix} \mu^1_{oil\_prod} & \mu^1_{gas\_prod} & \mu^1_{water\_prod} & \mu^1_{water\_inj} - \mu^1_{water\_prod} \\ \mu^2_{oil\_prod} & \mu^2_{gas\_prod} & \mu^2_{water\_prod} & \mu^2_{water\_inj} - \mu^2_{water\_prod} \\ \mu^3_{oil\_prod} & \mu^3_{gas\_prod} & \mu^3_{water\_prod} & \mu^3_{water\_inj} - \mu^3_{water\_prod} \\ 1 & 1 & 1 & 0 \end{bmatrix} \begin{bmatrix} \alpha_{oil} \\ \alpha_{gas} \\ \alpha_{water} \\ w \end{bmatrix};$$

$$\begin{bmatrix} \mu^1_{mix} \\ \mu^2_{mix} \\ \mu^3_{mix} \\ 1 \end{bmatrix} = \begin{bmatrix} \mu^1_{oil\_prod} & \mu^1_{water\_prod} & \mu^1_{gas\_prod} & \mu^1_{gas\_inj} - \mu^1_{gas\_prod} \\ \mu^2_{oil\_prod} & \mu^2_{water\_prod} & \mu^2_{gas\_prod} & \mu^2_{gas\_inj} - \mu^2_{gas\_prod} \\ \mu^3_{oil\_prod} & \mu^3_{water\_prod} & \mu^3_{gas\_prod} & \mu^3_{gas\_inj} - \mu^3_{gas\_prod} \\ 1 & 1 & 1 & 0 \end{bmatrix} \begin{bmatrix} \alpha_{oil} \\ \alpha_{water} \\ \alpha_{gas} \\ w \end{bmatrix};$$

and $$\begin{bmatrix} \mu^1_{mix} \\ \mu^2_{mix} \\ \mu^3_{mix} \\ 1 \end{bmatrix} = \begin{bmatrix} \mu^1_{water\_prod} & \mu^1_{gas\_prod} & \mu^1_{oil\_prod} & \mu^1_{oil\_inj} - \mu^1_{oil\_prod} \\ \mu^2_{water\_prod} & \mu^2_{gas\_prod} & \mu^2_{oil\_prod} & \mu^2_{oil\_inj} - \mu^2_{oil\_prod} \\ \mu^3_{water\_prod} & \mu^3_{gas\_prod} & \mu^3_{oil\_prod} & \mu^3_{oil\_inj} - \mu^3_{oil\_prod} \\ 1 & 1 & 1 & 0 \end{bmatrix} \begin{bmatrix} \alpha_{water} \\ \alpha_{gas} \\ \alpha_{oil} \\ w \end{bmatrix}.$$

3. The method of claim 1, wherein w is calculated using at least one of the following equations:

$$w = \frac{Volume_{water\_inj}}{Volume_{water\_inj} + Volume_{water\_prod}};$$

$$w = \frac{Volume_{gas\_inj}}{Volume_{gas\_inj} + Volume_{gas\_prod}}; \text{ and}$$

$$w = \frac{Volume_{oil\_inj}}{Volume_{oil\_inj} + Volume_{oil\_prod}}.$$

4. The method of claim 1, wherein the multiphase fluid is an effluent of a hydrocarbon fluid production comprising crude oil, natural gas and water, a phase fraction for crude oil is in the range of 0-1, a phase fraction for natural gas is in the range of 0-1, and a phase fraction for water is in the range of 0-1.

5. A method for measuring a composition of a multiphase fluid, the method comprising:
   radiating a photon beam through the multiphase fluid;
   measuring radiation absorption by the multiphase fluid for at least three energy levels to obtain measured radiation absorption data;
   providing the measured radiation absorption data to a processing unit; and
   calculating the composition of the multiphase fluid using the measured radiation absorption data and linear attenuation coefficients for components of the multiphase fluid, wherein the components include a produced fluid and an injected fluid of the same phase and calculating the composition of the multiphase fluid includes calculating the ratio of the volume of the injected fluid in the multiphase fluid to the sum of the volumes of the injected fluid and the produced fluid of the same phase in the multiphase fluid using the measured radiation absorption data and linear attenuation coefficients for the produced fluid and the injected fluid of the same phase.

6. The method of claim 5, wherein calculating the ratio of the volume of the injected fluid in the multiphase fluid to the sum of the volumes of the injected fluid and the produced fluid of the same phase in the multiphase fluid includes calculating the ratio of the volume of an injected water in the multiphase fluid to the sum of the volumes of the injected water and a produced water in the multiphase fluid.

7. The method of claim 5, wherein calculating the ratio of the volume of the injected fluid in the multiphase fluid to the sum of the volumes of the injected fluid and the produced fluid of the same phase in the multiphase fluid includes calculating the ratio of the volume of an injected gas in the multiphase fluid to the sum of the volumes of the injected gas and a produced gas in the multiphase fluid.

8. The method of claim 5, wherein calculating the ratio of the volume of the injected fluid in the multiphase fluid to the sum of the volumes of the injected fluid and the produced fluid of the same phase in the multiphase fluid includes calculating the ratio of the volume of an injected oil-solvent mixture in the multiphase fluid to the sum of the volumes of the injected oil-solvent mixture and a produced oil in the multiphase fluid.

9. The method of claim 5, comprising calculating water cut for the multiphase fluid.

10. The method of claim 5, wherein the produced fluid and the injected fluid of the same phase include a produced water and an injected water, and the method comprises:
   calculating mass attenuation coefficients at different energy levels for the produced water using a mass fraction of total salt in the produced water and proportions of particular ion-salts in the total salt; and
   calculating linear attenuation coefficients for the produced water using the calculated mass attenuation coefficients for the produced water.

11. The method of claim 5, wherein the produced fluid and the injected fluid of the same phase include a produced water and an injected water, and the method comprises:
   calculating mass attenuation coefficients at different energy levels for the injected water using a mass fraction of total salt in the injected water and proportions of particular ion-salts in the total salt; and
   calculating linear attenuation coefficients for the injected water using the calculated mass attenuation coefficients for the injected water.

* * * * *